US009028875B2

(12) United States Patent
Kwon et al.

(10) Patent No.: US 9,028,875 B2
(45) Date of Patent: May 12, 2015

(54) IRON OXIDE NANOCAPSULE, METHOD OF MANUFACTURING THE SAME, AND MRI CONTRAST AGENT USING THE SAME

(75) Inventors: Eun Byul Kwon, Daejeon (KR); Bong-Sik Jeon, Daejeon (KR); Eung Gyu Kim, Daejeon (KR); Ju Young Park, Daejeon (KR); Wan Jae Myeong, Daejeon (KR)

(73) Assignee: Hanwha Chemical Corporation, Seoul (KR)

( * ) Notice: Subject to any disclaimer, the term of this patent is extended or adjusted under 35 U.S.C. 154(b) by 275 days.

(21) Appl. No.: 13/818,734

(22) PCT Filed: Aug. 31, 2011

(86) PCT No.: PCT/KR2011/006468
§ 371 (c)(1), (2), (4) Date: Apr. 25, 2013

(87) PCT Pub. No.: WO2012/030166
PCT Pub. Date: Mar. 8, 2012

(65) Prior Publication Data

US 2014/0328768 A1 Nov. 6, 2014

(30) Foreign Application Priority Data

Aug. 31, 2010 (KR) ........................ 10-2010-0084756

(51) Int. Cl.

| | |
|---|---|
| *A61B 5/055* | (2006.01) |
| *A61K 49/18* | (2006.01) |
| *A61K 49/12* | (2006.01) |
| *B82Y 5/00* | (2011.01) |
| *B01J 13/06* | (2006.01) |

(52) U.S. Cl.
CPC ........... *A61K 49/1863* (2013.01); *A61K 49/128* (2013.01); *A61K 49/1851* (2013.01); *A61K 49/1818* (2013.01); *A61K 49/1827* (2013.01); *A61K 49/12* (2013.01); *A61K 49/126* (2013.01); *B82Y 5/00* (2013.01); *B01J 13/06* (2013.01)

(58) Field of Classification Search
None
See application file for complete search history.

(56) References Cited

U.S. PATENT DOCUMENTS

| | | | |
|---|---|---|---|
| 6,861,064 | B1 | 3/2005 | Laakso et al. |
| 7,811,545 | B2 | 10/2010 | Hyeon et al. |
| 2006/0222594 | A1 | 10/2006 | Lee et al. |

FOREIGN PATENT DOCUMENTS

| | | | |
|---|---|---|---|
| KR | 1020010031289 | A | 4/2001 |
| KR | 1020040092969 | A | 11/2004 |
| KR | 1020060084702 | A | 7/2006 |
| KR | 1020090085834 | A | 8/2009 |
| WO | 2006057533 | A1 | 6/2006 |

*Primary Examiner* — James Rogers
(74) *Attorney, Agent, or Firm* — The Webb Law Firm

(57) ABSTRACT

Provided is an iron oxide nanocapsule which has extremely excellent water dispersibility, which is very stable in the body and which has very excellent MRI contrast ability, a method of manufacturing the same, and an MRI contrast agent using the same. The method of manufacturing the iron oxide nanocapsule includes the steps of: thermally decomposing an iron complex to prepare hydrophobic ligand-bonded iron oxide nanoparticles; and encapsulating the hydrophobic ligand-bonded iron oxide nanoparticles by a carboxymethyldextran-dodecylamine conjugate encapsulation material or a dextran-linoleic acid conjugate encapsulation material to form an iron oxide nanocapsule.

19 Claims, 11 Drawing Sheets

(BEFORE INJECTING CONTRAST AGENT) (AFTER INJECTING CONTRAST AGENT)

(BEFORE INJECTING CONTRAST AGENT) (AFTER INJECTING CONTRAST AGENT)

IRON OXIDE NANOCAPSULE, METHOD OF MANUFACTURING THE SAME, AND MRI CONTRAST AGENT USING THE SAME

TECHNICAL FIELD

The present invention relates to an iron oxide nanocapsule which has extremely excellent water dispersibility, which is stable in the body and which has excellent MRI contrast ability, a method of manufacturing the same, and an MRI contrast agent using the same.

BACKGROUND ART

Nanomaterials are materials having a size of 1 nm~100 nm. They can be synthesized in various shapes such as a sphere, plate, tube and the like. Since nanomaterials have peculiar properties different from conventional bulk materials, applied technologies using such peculiar properties of nanomaterials have been actively developed in various fields of electronics, information, environment, energy, medicine, etc.

Particularly, among nanomaterials, magnetic nanoparticles having magnetic properties have been widely researched for the purpose of biomaterial extraction, magnetic resonance imaging (MRI) contrast agents, biosensors, drug/gene transfer, and high-temperature magnetic medical treatment. Among MRI contrast agents, an MRI liver contrast agent based on iron oxide nanoparticles, Resovist (manufactured by Bayer Schering Corporation), is currently used in clinical practice, and an MRI lymph node contrast agent, Combidex (manufactured by AMAAG Corporation), is known to be under clinical testing.

However, iron oxide nanoparticles, which are magnetic nanoparticles used for commercially-available MRI contrast agents, are synthesized by coprecipitation using a metal salt in an aqueous solution. Therefore, the iron oxide nanoparticles synthesized in this way are disadvantageous in that it is difficult to adjust their size, and in that they have poor monodispersity. Further, since these iron oxide nanoparticles are synthesized at room temperature, there is a disadvantage in that they have low crystallinity.

Further, iron oxide nanoparticles may also be synthesized by thermal decomposition. Thermal decomposition. uses a process of mixing an organic surface stabilizer with an organic solvent and a metal precursor to improve particle stability and then heating the mixture to the boiling point of the organic solvent to age the mixture. Therefore, thermal decomposition is advantageous in that a reaction temperature can be easily controlled, and in that iron oxide nanoparticles of various sizes can be synthesized when solvents having boiling points different from each other are used. The iron oxide nanoparticles synthesized in this way exhibit excellent physical properties in application fields because they have excellent monodisperity and crystallinity compared to iron oxide nanoparticles synthesized in an aqueous solution.

However, thermal decomposition is problematic in that iron oxide nanoparticles are synthesized in an organic solvent, so that the synthesized iron oxide nanoparticles are surrounded by an organic substance, with the result that these iron oxide nanoparticles are not suitable for practical use in nano-bio applications.

Therefore, it is required to surface-treatment the iron oxide nanoparticles using a water-dispersible material that is stable in the body. There are various methods of surface-treatment of nanoparticles. Typically, there are ligand exchange methods of converting the organic substance surrounding nanoparticles into a hydrophilic substance and encapsulation methods of covering nanoparticles with a hydrophilic substance with the nanoparticles surrounded by the organic substance. The encapsulation methods include a method of capsulating one nanoparticle and a method of capsulating several nanoparticles.

In the encapsulation methods, when an amphiphilic compound having both hydrophilicity and hydrophobicity is used, the hydrophobic region of the amphiphilic compound bonds with the surface of nanoparticles, and the hydrophilic region thereof is distributed throughout the outermost shell of the encapsulated nanoparticles, so that water-insoluble nanoparticles can be stably dispersed in an aqueous solution, thereby maximizing the usage rate of nanoparticles in the body.

SUMMARY OF INVENTION

Technical Problem

An object of the present invention is to provide an iron oxide nanocapsule which has extremely excellent water dispersibility, which is very stable in the body and which has very excellent MRI contrast ability, and a method of manufacturing the same.

Technical Solution

In order to accomplish the above object, an aspect of the present invention provides a method of manufacturing an iron oxide nanocapsule, comprising the steps of: thermally decomposing an iron complex to prepare hydrophobic ligand-bonded iron oxide nanoparticles; and encapsulating the hydrophobic ligand-bonded iron oxide nanoparticles by a carboxymethyldextran-dodecylamine conjugate encapsulation material or a dextran-linoleic acid conjugate encapsulation material to form an iron oxide nanocapsule.

Another aspect of the present invention provides an iron oxide nanocapsule, manufactured by the method.

Still another aspect of the present invention provides a magnetic resonance imaging (MRI) contrast agent, comprising the iron oxide nanocapsule.

Advantageous Effects

The method of manufacturing an iron oxide nanocapsule according to the present invention is characterized in that a plurality of iron oxide nanoparticles are encapsulated by a single nanocapsule, so that these iron nanoparticles conglomerate each other, thereby causing the iron oxide nanocapsule to have very excellent magnetic resonance imaging (MRI) contrast ability, and is advantageous in that, since the iron oxide nanocapsules manufactured by this method are uniform in size, it is possible to prevent these iron oxide nanocapsules from being absorbed and distributed into organs other than the targeted organs (particularly, the liver), and these iron oxide nanocapsules have extremely excellent dispersibility to an aqueous solution and are stable in the body.

DESCRIPTION OF DRAWINGS

The above and other objects, features and advantages of the present invention will become apparent from the following description of preferred embodiments given in conjunction with the accompanying drawings, in which:

FIG. 13 is a TEM photograph of carboxymethyldextran-iron oxide nanoparticles prepared in Comparative Example 1;

FIG. 14 is a TEM photograph of carboxymethyldextran-iron oxide nanoparticles prepared in Comparative Example 2;

BEST MODE

Figure 1:
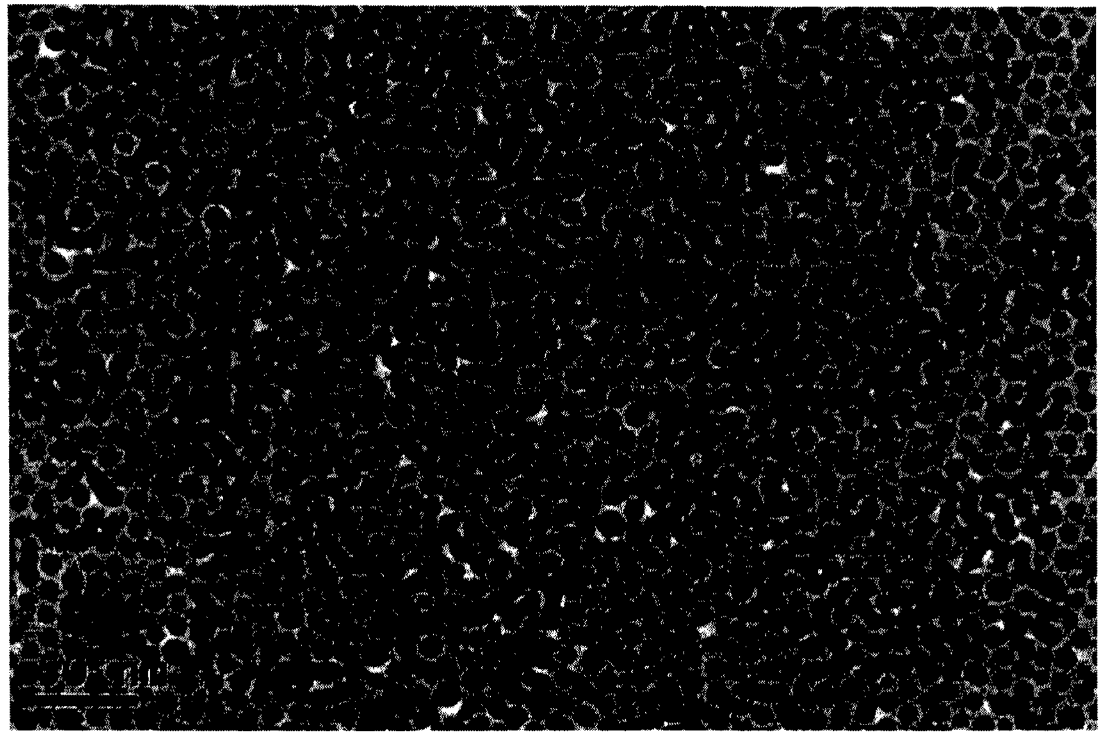
FIG. 1 is a transmission electron microscope (TEM) photograph of iron oxide nanoparticles prepared in Preparation Example 1.

Hereinafter, preferred embodiments of the present invention will be described in detail with reference to the accompanying drawings.

The following drawings are provided for those skilled in the art as examples in order to sufficiently explain the technical idea of the present invention. Therefore, the present invention may be modified in various forms without being limited to the following drawings, and these drawings may be exaggerated to clearly explain the technical idea of the present invention. Further, the same reference numerals are used throughout the accompanying drawings to designate the same or similar components.

In this case, the technical and scientific terms used in the present specification are generally understood by those skilled in the art as long as they are not differently defined. Further, in the description of the present invention, when it is determined that the detailed description of the related art would obscure the gist of the present invention, the description thereof will be omitted.

The method of manufacturing an iron oxide nanocapsule according to the present invention includes the steps of: thermally decomposing an iron complex to prepare hydrophobic ligand-bonded iron oxide nanoparticles; and encapsulating the hydrophobic ligand-bonded iron oxide nanoparticles in a carboxymethyldextran-dodecylamine conjugate encapsulation material or a dextran-linoleic acid conjugate encapsulation material to form an iron oxide nanocapsule.

Concretely, the method of manufacturing an iron oxide nanocapsule according to the present invention includes the steps of: a) preparing a carboxymethyldextran-dodecylamine conjugate encapsulation material represented by Formula 1 below or a dextran-linoleic acid conjugate encapsulation material represented by Formula 2 below; b) thermally decomposing an iron complex in which a hydrophobic organic acid group of $C_4$ to $C_{25}$ as a ligand is bound to iron as a central atom to prepare hydrophobic ligand-bonded iron oxide nanoparticles; c) dissolving the encapsulation material in a buffer solution to prepare an aqueous solution of the encapsulation material, and dispersing the iron oxide nanoparticles in an organic nonpolar solvent to prepare a nanoparticle-dispersed solution; dropping the nanoparticle-dispersed solution into the aqueous solution of encapsulation material and stirring a mixed solution of the aqueous solution of encapsulation material and the nanoparticle-dispersed to prepare an iron oxide nanocapsule-dispersed solution in which iron oxide nanocapsules each encapsulating a plurality of the iron oxide nanoparticles are dispersed; and e) removing the organic nonpolar solvent from the iron oxide nanocapsule-dispersed solution by volatilization to prepare a water-dispersed iron oxide nanocapsule solution.

[Formula 2]

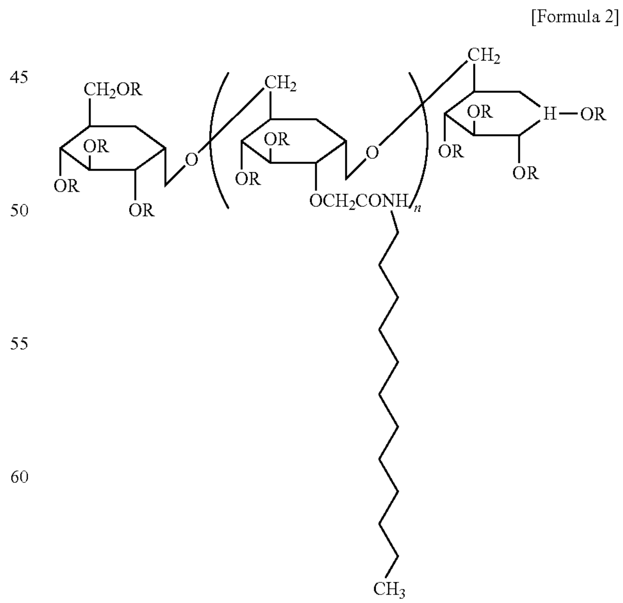

wherein R is H or $CH_2COOH$, and n is an integer of 1 to 5000.

[Formula 2]

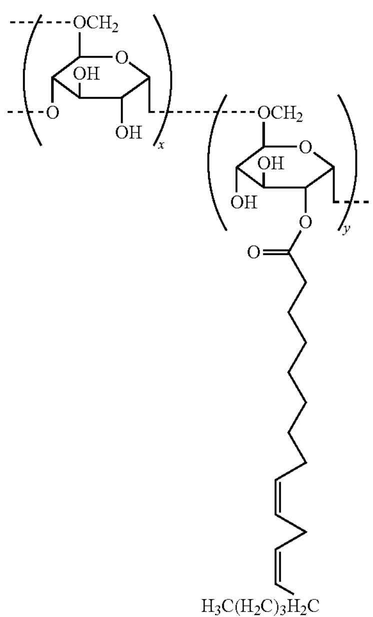

wherein x is an integer of 1 to 1000, and y is an integer of 1 to 1000.

The carboxymethyldextran-dodecylamine conjugate encapsulation material represented by Formula 1 above or the dextran-linoleic acid conjugate encapsulation material represented by Formula 2 above forms micelles in aqueous solution. Therefore, this encapsulation material is characterized in that it can encapsulate the hydrophobic ligand-bonded iron oxide nanoparticles synthesized by thermal decomposition to have a uniform size, and the encapsulated iron oxide nanocapsules have extremely excellent dispersibility in an aqueous solvent.

Further, the iron oxide nanoparticles prepared by thermally decomposing an iron complex in which a hydrophobic organic acid group of $C_4$ to $C_{25}$ as a ligand is bound to iron as a central atom are characterized in that their sizes can be precisely controlled to a range of several nanometers to several tens of nanometers depending on the thermal decomposition temperature and time, and they have very uniform sizes.

Meanwhile, dextran, which is a water-soluble polysaccharide containing glucose (one of the D-glucoses), serves to polymerize the D-glucoses by decomposing sucrose using lactic bacteria belonging to Leuconostoc. Dextran, which is a material approved by the FDA, is used as a plasma expander, and, particularly, has been used as a material for coating iron oxide nanoparticles of a commonly-used MRI contrast agent (Feridex, manufactured by AMAG Corp.). Carboxymethyldextran is a dextran derivative which is dextran bonded with a carboxyl group. It is known that 1.1~1.5 mmol of a carboxyl group is bonded with 1 g of carboxymethyldextran. Carboxymethyldextran is used as a material for coating iron oxide nanoparticles of Resovist, which is a commonly-used iron oxide nanoparticle-based contrast agent, and has been used as a material for coating iron oxide nanoparticles of Combidex, which is a lymph node contrast agent that is undergoing clinical testing. Therefore, iron oxide nanoparticles, which have very excellent dispersibility in an aqueous solvent and are very stable in the body, are prepared, and these iron oxide nanoparticles are encapsulated by the carboxymethyldextran-dodecylamine conjugate represented by Formula 1 above or the dextran-linoleic acid conjugate represented by Formula 2 above to manufacture iron oxide nanocapsules having an extremely uniform size, thereby preventing capillary vessels from being clogged by these iron oxide nanocapsules or preventing these iron oxide nanocapsules from being absorbed and diffused into tissues other than the targeted tissues.

Concretely, in the method according to a first embodiment of the present invention, the encapsulation material is a carboxymethyldextran-dodecylamine conjugate, and the step a) includes the steps of: a1-1) mixing a carboxymethyldextran solution with a dodecylamine solution to form a first mixed solution; a1-2) adding 1-ethyl-3-(3-dimethylaminopropyl) carbodiimide (EDC) and n-hydroxysuccinicimide (NHS) to the first mixed solution to form a second mixed solution; and a1-3) dialyzing, freeze-drying the second mixed solution.

The carboxymethyldextran has an average molecular weight of 500~1,000,000 Da, preferably 10,000~100,000 Da.

The carboxymethyldextran solution may be prepared by adding dimethyl sulfoxide (DMSO) to an aqueous carboxymethyldextran solution in which carboxymethyldextran is mixed with water at a ratio of 1(carboxymethyldextran):3~5 (water) by weight, the dimethyl sulfoxide (DMSO) being added in an amount of 10 to 15 times that of water in the aqueous carboxymethyldextran solution by weight. The dodecylamine solution may be prepared by mixing dodecylamine, chloroform and dimethyl sulfoxide (DMSO) at a ratio of 1:8~12:25~35 by weight.

In the step a1-1), the carboxymethyldextran solution may be mixed with the dodecylamine solution such that a ratio of dodecylamine:carboxymethyldextran is 1:1~10 by weight. In this case, the hydrophilicity and hydrophobicity of the carboxymethyldextran-dodecylamine conjugate prepared by mixing the carboxymethyldextran solution with the dodecylamine solution can be controlled.

Subsequently, in the step a1-2), the dodecylamine, EDC and NHS may be added such that a ratio of dodecylamine: EDC:NHS is 1:0.3~0.7:0.1~0.4 by weight.

Concretely, in the method according to a second embodiment of the present invention, the encapsulation material is a dextran-linoleic acid conjugate, and the step a) includes the steps of: a2-1) mixing a dextran solution with a linoleic acid solution to form a first mixed solution; a2-2) adding n,n'-dicyclohexylcarbodiimide (DCC) and dimethylaminopyridine (DMAP) to the first mixed solution to form a second mixed solution; and a2-3) dialyzing, freeze-drying the second mixed solution.

The dextran has an average molecular weight of 100~100,000 Da, preferably 5,000~10,000 Da.

The dextran solution may be prepared by mixing dextran and dimethyl sulfoxide (DMSO) at a ratio of 1:50~80 by weight, and the linoleic acid solution may be prepared by mixing linoleic acid and dimethyl sulfoxide (DMSO) at a ratio of 1:8~14 by weight.

In the step a2-1), the dextran solution may be mixed with the linoleic acid solution such that a ratio of dextran:linoleic acid is 1:2~5 by weight. In this case, the hydrophilicity and hydrophobicity of the dextran-linoleic acid conjugate prepared by mixing the carboxymethyldextran solution with the dodecylamine solution can be controlled.

Subsequently, in the step a2-2), the dextran, DCC and DMAP may be added such that a ratio of dextran:DCC: DMAP is 1:1.5~2:0.3~0.8 by weight. In this case, the DCC and DMAP may be added with each of them dissolved in DMSO.

In the method of manufacturing an iron oxide nanocapsule according to the present invention (including first and second embodiments), in the step c), the buffer solution may be a phosphate buffered saline (PBS), and the organic nonpolar solvent may be chloroform.

The aqueous solution of encapsulation material may be prepared by mixing the encapsulation material with the buffer solution at a ratio of 1:50~500 by weight, and the nanoparticle-dispersed solution may be prepared by mixing iron oxide nanoparticles with the organic nonpolar solvent at a ratio of 1:10~100 by weight.

The amount of iron oxide nanoparticles encapsulated by a single nanocapsule, the average size of nanocapsules, the size distribution of nanocapsules and the degree of aggregation of iron oxide nanoparticles are controlled by the size of iron oxide nanoparticles and the conditions of the step d).

In order to exhibit the magnetic properties suitable for a contrast agent and maximize the MIR contrast ability, it is preferred that the average size (diameter) of the iron oxide nanoparticles be 3~20 nm. As described above, the iron oxide nanoparticles are hydrophobic ligand-bonded iron oxide nanoparticles prepared by thermally decomposing an iron complex in which a hydrophobic organic acid group of $C_4$ to $C_{25}$ as a ligand is bound to iron as a central atom. The iron complex includes an iron oleate complex, and the hydrophobic ligand-bonded iron oxide nanoparticles include oleate-bonded iron oxide nanoparticles.

Concretely, the iron oxide nanoparticles may be prepared by reacting the iron complex with aliphatic acid including oleic acid at 300~350° C. for 20~90 minutes. Referring to PCT/KR2005/004009, the method of preparing iron oxide nanoparticles will be described in more detail.

In order to decrease the deviation in the amounts of iron oxide nanoparticles encapsulated by nanocapsules and to effectively encapsulate iron oxide nanoparticles by nanocapsules, in the step d), an iron oxide nanoparticle-dispersed solution having a ratio of the encapsulation material:the iron oxide nanoparticles of 1:0.05~0.25 by weight may be dropped into the aqueous solution of encapsulation material.

In order to control the average size of nanocapsules within a range of 100~500 nm and to manufacture nanocapsule having a very uniform size, in the step d), the iron oxide nanoparticle-dispersed solution may be dropped into the aqueous solution of encapsulation material at a drip rate of 0.1~3 mL/min.

In the step d), the aqueous solution of encapsulation material is stirred at a rotational speed of 20000~30000 rpm. In this case, it is preferred that the iron oxide nanoparticle-dispersed solution be dropped into the aqueous solution of encapsulation material, and simultaneously stirred.

According to the above-mentioned method of manufacturing an iron oxide nanocapsule, iron oxide nanocapsules, in each of which hydrophobic ligand-bonded iron oxide nanoparticles having an average size of 5~20 nm are encapsulated by a carboxymethyldextran-dodecylamine conjugate encapsulation material or a dextran-linoleic acid conjugate encapsulation material, can be manufactured, and iron oxide nanocapsules having an average size of 100~500 nm and extremely excellent dispersibility in an aqueous solvent can be manufactured.

The MRI contrast agent including the iron oxide nanocapsules is suitable for a liver contrast agent. These iron oxide nanocapsules have excellent liver selectivity and very excellent contrast ability.

MODE FOR INVENTION

Hereinafter, the present invention will be described in more detail with reference to the following Examples. However, the scope of the present invention is not limited thereto.

Preparation Example 1

Preparation of 10 nm Iron Oxide Nanoparticles 10.8 g of iron chloride(III) hexahydrate ($FeCl_3.6H_2O$, 40 mmol) and 36.5 g of sodium oleate (120 mmol) were dissolved in a mixed solvent including ethanol 80 mL, distilled water 60 mL and hexane 140 mL to form a mixed solution, and then the mixed solution was heated to 57° C. and maintained at 57° C. for 1 hour. During this process, the initial scarlet of the mixed solution in an aqueous phase became clear, and the initially transparent mixed solution in an organic phase became reddish. It can be ascertained from this fact that an iron oleate complex was successfully synthesized.

After the reaction was completed, an organic layer including the iron oleate complex was separated from the mixed solution, and then hexane was volatilized. As a result, the mixed solution changed into a viscous liquid.

36 g of the synthesized iron oleate complex was added to a mixture of 200 g of octadecene and 5.7 g of oleic acid. The resultant mixture was heated from room temperature to 70° C. at a heating rate of 2.5° C./min in a vacuum, and then maintained at 70° C. for 1 hour to remove residual solvent and water excluding the reactants.

Thereafter, the resultant mixture was heated to 320° C. at a heating rate of 2.5° C./min under a nitrogen atmosphere, and then maintained at 320° C. for 30 minutes to be aged. During this process, a reaction was violently conducted, and the initial red solution became blackish brown. It can be ascertained from this fact that the iron oleate complex was completely decomposed, and iron oxide nanoparticles were produced.

After the reaction had been completed, the resultant solution including iron oxide nanoparticles was oxidized by injecting air when the temperature of this resultant solution was decreased to an autoignition temperature or lower (150° C.) by natural cooling. As a result, the resultant solution was cooled to room temperature, and black precipitates were produced by adding a mixed solution of hexane and acetone having a volume ratio of 1:5 to this resultant solution such that the amount of the mixed solution is three times that of the resultant solution by volume, and then the produced precipitates were separated using a centrifuge (rpm=2,000).

The washing process of adding the mixed solution of hexane and acetone and centrifugation was repeated at least two times, and hexane and acetone remaining in the resultant solution were removed by drying to prepare oleate-bonded iron oxide nanoparticles which were easily re-dispersed in hexane.

FIG. 1 is a transmission electron microscope (TEM) photograph of the prepared iron oxide nanoparticles. From FIG. 1, it was ascertained that oleate-bonded iron oxide nanoparticles having an average diameter of 10 nm were prepared, and that spherical iron oxide nanoparticles having a uniform particle size were prepared.

Preparation Example 2

Preparation of 11 nm Iron Oxide Nanoparticles

Iron oxide nanoparticles were prepared using the same reaction conditions as Preparation Example 1, except that the aging time was 1 hour in the synthesis process.

Figure 2:
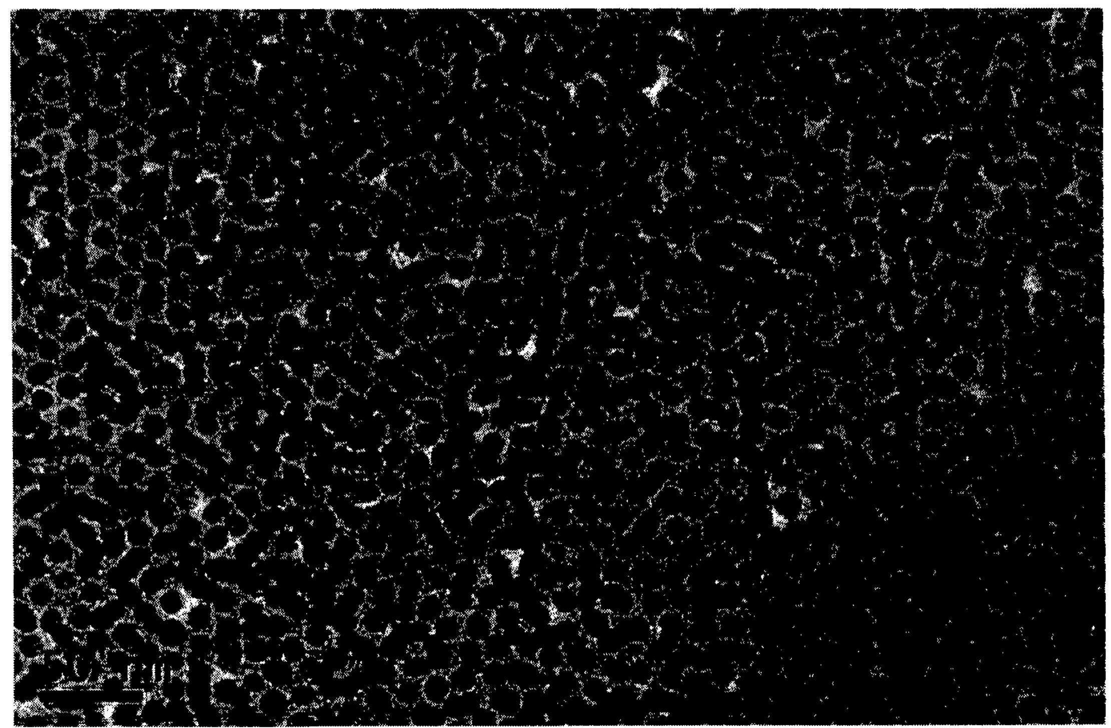
FIG. 2 is TEM photograph of iron oxide nanoparticles prepared in Preparation Example 2.

FIG. 2 is a transmission electron microscope (TEM) photograph of the prepared iron oxide nanoparticles. From FIG. 2, it was ascertained that oleate-bonded iron oxide nanoparticles having an average diameter of 11 nm were prepared, and that spherical iron oxide nanoparticles having a very uniform particle size were prepared.

Preparation Example 3

Preparation of 15 nm Iron Oxide Nanoparticles

Iron oxide nanoparticles were prepared using the same reaction conditions as Preparation Example 1, except that 1-eicosene was used instead of octadecene, and aging was performed at 330° C. for 1 hour in the synthesis process.

Figure 3:
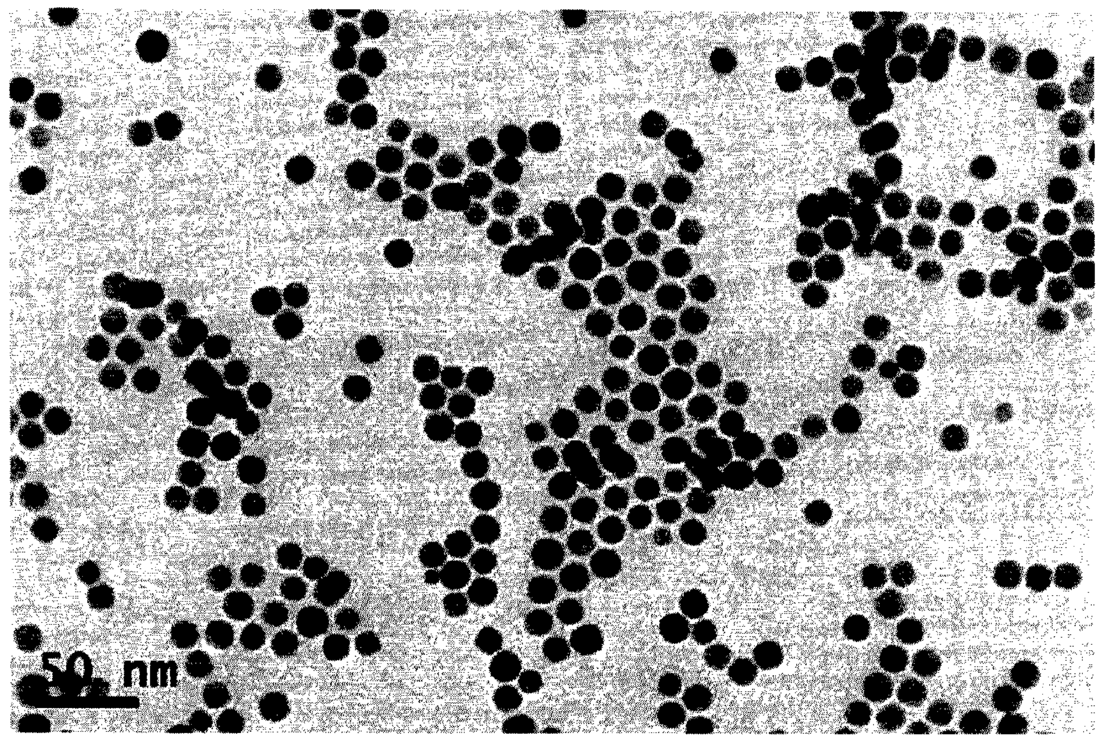
FIG. 3 is TEM photograph of iron oxide nanoparticles prepared in Preparation Example 3.

FIG. 3 is a transmission electron microscope (TEM) photograph of the prepared iron oxide nanoparticles. From FIG. 3, it was ascertained that oleate-bonded iron oxide nanoparticles having an average diameter of 15 nm were prepared, and that spherical iron oxide nanoparticles having a very uniform particle size were prepared.

Example 1

Synthesis of Carboxymethyldextran-Dodecylamine Conjugate

In order to synthesize a carboxymethyldextran-dodecylamine conjugate, 5 g of carboxymethyldextran (average molecular weight: 14000 Da) was completely dissolved in 20 mL of distilled water, and then mixed with 250 mL of dimethylsulfoxide (DMSO) to prepare a carboxymethyldextran solution. Further, 1.4 g (7.5 mmol) of dodecylamine and 10 mL of chloroform ($CHCl_3$) were mixed with 40 mL of dimethylsulfoxide (DMSO) to prepare a dodecylamine solution.

The two solutions were mixed with each other by dropping the dodecylamine solution into the carboxymethyldextran solution, and then an EDC solution in which 0.7 g of EDC (1-Ethyl-3-(3-dimethylaminopropyl)carbodiimide) was completely dissolved in 30 ml of DMSO, and an NHS solution in which 0.35 g of NHS (n-hydroxysuccinicimide) was completely dissolved in 10 mL of DMSO, were injected into the mixed solution.

Thereafter, the resultant mixed solution was stirred at room temperature for 24 hours and then filtered using filter paper, and then an excessive amount of ethanol was added to the filtered mixed solution to produce a white precipitate. This white precipitate was separated using centrifuge (rpm=3,000).

This precipitate was dispersed in distilled water, dialyzed for 3 days, and then freeze-dried to obtain a white solid carboxymethyldextran-dodecylamine conjugate.

Figure 4:
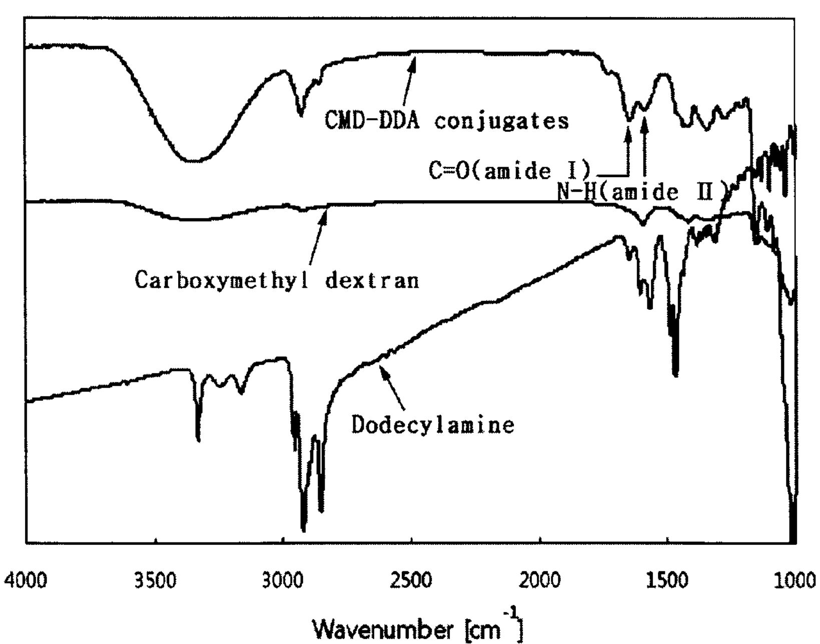
FIG. 4 is a graph showing the results of FT-IR analysis of a carboxymethyldextran-dodecylamine amphiphilic polymer composite prepared in Example 1.

FIG. 4 is a graph showing the results of FT-IR analysis of a carboxymethyldextran-dodecylamine amphiphilic polymer composite. As shown in FIG. 4, new peaks appeared at 1656 $cm^{-1}$ and 1593 $cm^{-1}$. These new peaks mean C=O stretching (amide I) and N—H deformation (amide II) of an amide bond. Further, C—H stretching peaks appeared at 2933 $cm^{-1}$ and 2875 $cm^{-1}$. Based on these results, it can be ascertained that a carboxymethyldextran-dodecylamine conjugate was successfully synthesized.

Example 2

Encapsulation of Iron Oxide Nanoparticles Using Carboxymethyldextran-Dodecylamine Conjugate 55 mg of the carboxymethyldextran-dodecylamine conjugate synthesized in Example 1 and 25 ml of PBS were mixed, and then ultrasonically treated for 10 minutes to obtain an aqueous solution of encapsulation material. Further, 11 mg of the iron oxide nanoparticles having an average particle size of 10 nm, prepared in Preparation Example 1, was dispersed in 0.5 mL of chloroform, and then ultrasonically treated for 10 minutes to obtain an iron oxide nanoparticle-dispersed solution.

The iron oxide nanoparticle-dispersed solution was dropped into the aqueous solution of encapsulation material (carboxymethyldextran-dodecylamine conjugate solution) at a drip rate of 1 mL/min, and simultaneously these solutions were mixed with each other for 10 minutes using a homogenizer (rpm=26,000) to form nanocapsule particles. Subsequently, chloroform was removed from the solution containing the nanocapsule particles using a vacuum evaporator.

Figure 5:
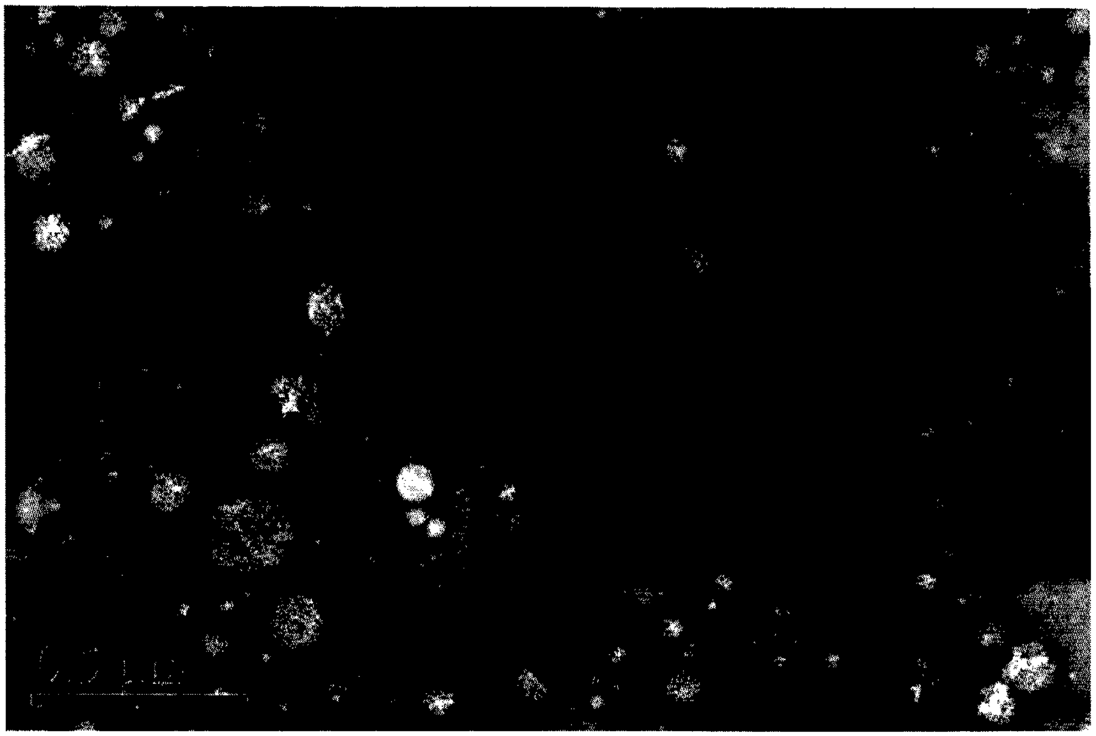
FIG. 5 is a TEM photograph of iron oxide nanocapsules, in each of which oleate-bonded iron oxide nanoparticles are encapsulated by a carboxymethyldextran-dodecylamine conjugate encapsulation material prepared in Example 2.

FIG. 5 is a TEM photograph of iron oxide nanocapsules, in each of which oleate-bonded iron oxide nanoparticles are encapsulated by the prepared carboxymethyldextran-dodecylamine conjugate encapsulation material, after negative staining. It can be ascertained from FIG. 5 that iron oxide nanoparticles were encapsulated, and that a plurality of iron oxide nanoparticles were encapsulated by a single nanocapsule. The sizes of nanocapsules were measured by dynamic light scattering (DLS, manufactured by Melvern Corp.). As a result, it was ascertained that the average particle size of the iron oxide nanocapsules was 150 nm.

Example 3

Figure 6:
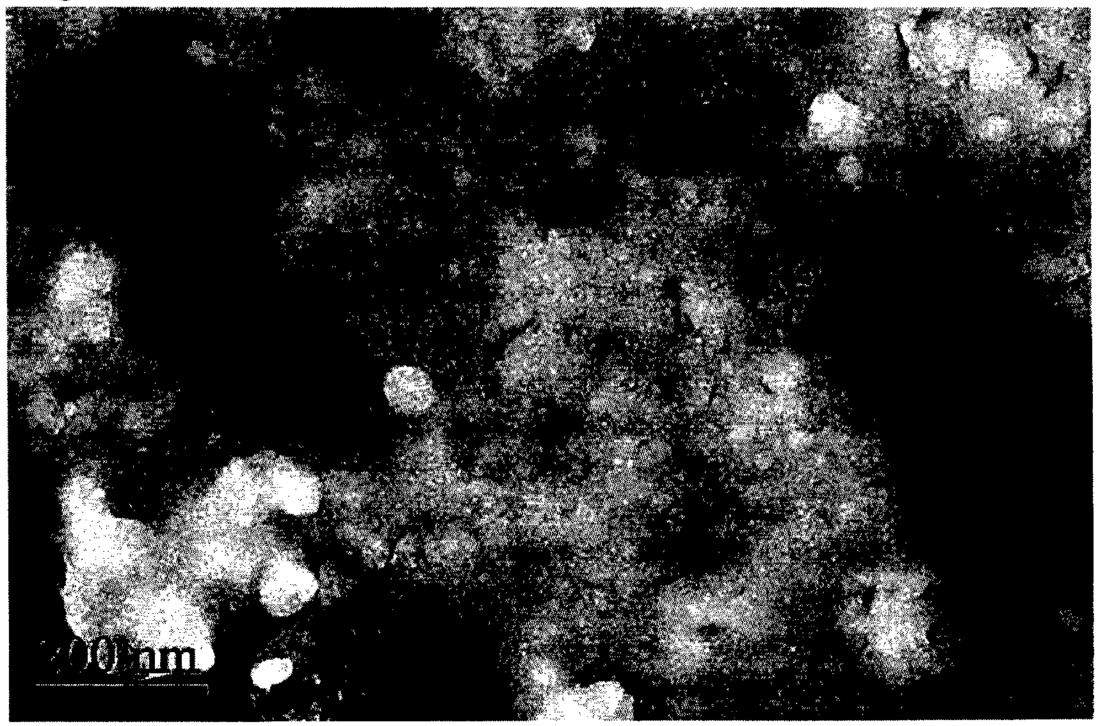
FIG. 6 is a TEM photograph of iron oxide nanocapsules manufactured in Example 3.

Encapsulation of Iron Oxide Nanoparticles Using Carboxymethyldextran-Dodecylamine Conjugate Nanocapsule particles were manufactured in the same manner as Example 2, except that the iron oxide nanoparticles having an average particle size of 11 nm, prepared in Preparation Example 2, were used. FIG. 6 is a TEM photograph of iron oxide nanocapsules manufactured in Example 3. The average particle size of the manufactured iron oxide nanocapsules was 144 nm.

Example 4

Figure 7:
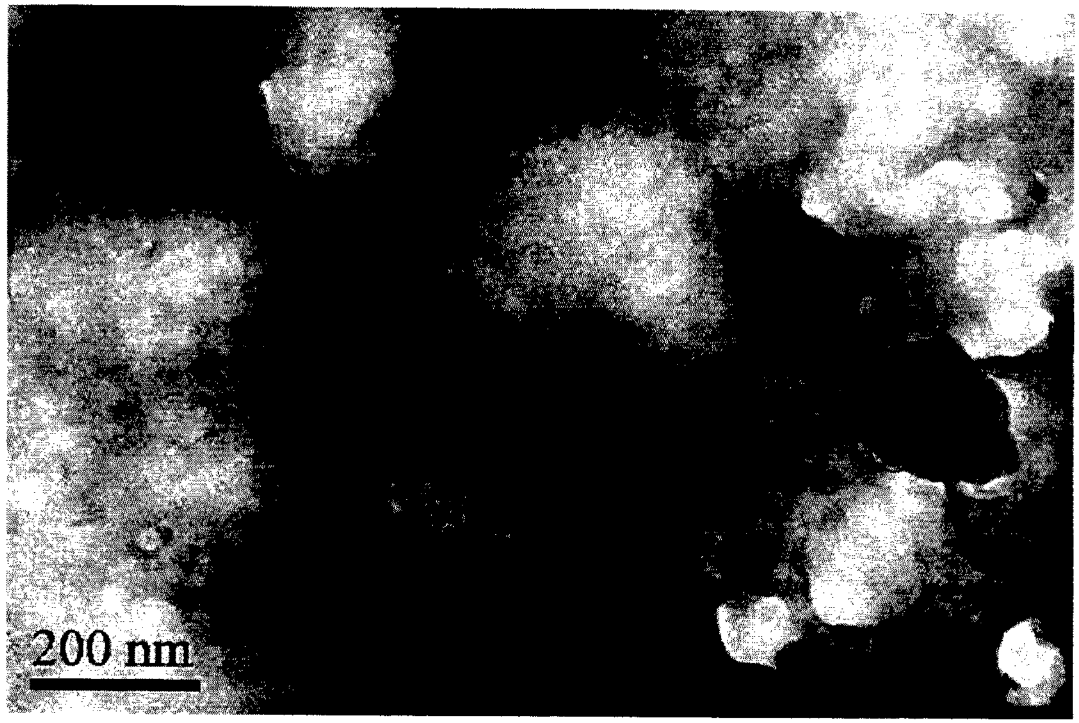
FIG. 7 is a TEM photograph of iron oxide nanocapsules manufactured in Example 4.

Encapsulation of Iron Oxide Nanoparticles Using Carboxymethyldextran-Dodecylamine Conjugate Nanocapsule particles were manufactured in the same manner as Example 2, except that the iron oxide nanoparticles having an average particle size of 15 nm, prepared in Preparation Example 3, were used. FIG. 7 is a TEM photograph of iron oxide nanocapsules manufactured in Example 4. The average particle size of the manufactured iron oxide nanocapsules was 188 nm.

Example 5

Measurement of In-Vitro Magnetic Resonance Relaxivity of Iron Oxide Nanocapsules The nanocapsules manufactured in Examples 2, 3 and 4 were respectively dispersed in PBS to form a nanocapsule solution having a nanocapsule concentration of 0.36 μg/mL, a nanocapsule solution having a nanocapsule concentration of 0.19 μg/mL and a nanocapsule solution having a nanocapsule concentration of 0.12 μg/mL. Then, five nanocapsule solutions having different nanocapsule concentrations from each other were prepared with respect to each sample, and then the in-vitro magnetic resonance relaxivities of these nanocapsule solutions were measured using a 4.7 T magnetic resonance imaging apparatus (Biospec 47/40, Bruker Biospin MRI GmbH). Further, the T2 relaxing times thereof were measured using MSME (Multi Slice Multi Echo sequence), and the detailed parameters thereof are shown in Table 1 below.

TABLE 1

| Class. | Parameters | Remark |
|---|---|---|
| TR (Repetition time) | 10,000 ms | |
| TE (Echo time) | 8~2048 ms | 256 times at 8 ms intervals |
| FOV | 60 × 40 mm | |
| Resolution | 0.234 × 0.156 mm/pixel | |

Figure 8:
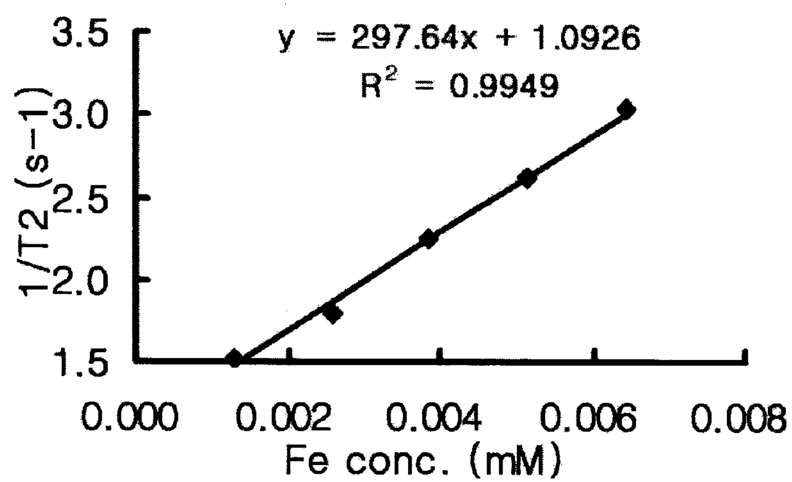
FIG. 8 is a graph showing the results of measuring the R2 relaxivity of an iron oxide nanocapsule encapsulating iron oxide nanoparticles having a size of 10 nm.
Figure 9:
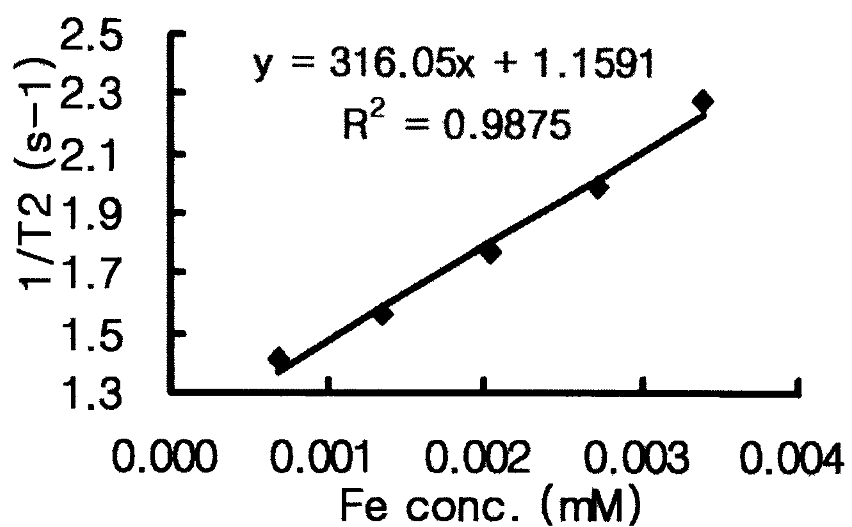
FIG. 9 is a graph showing the results of measuring the R2 relaxivity of an iron oxide nanocapsule encapsulating iron oxide nanoparticles having a size of 11 nm.
Figure 10:
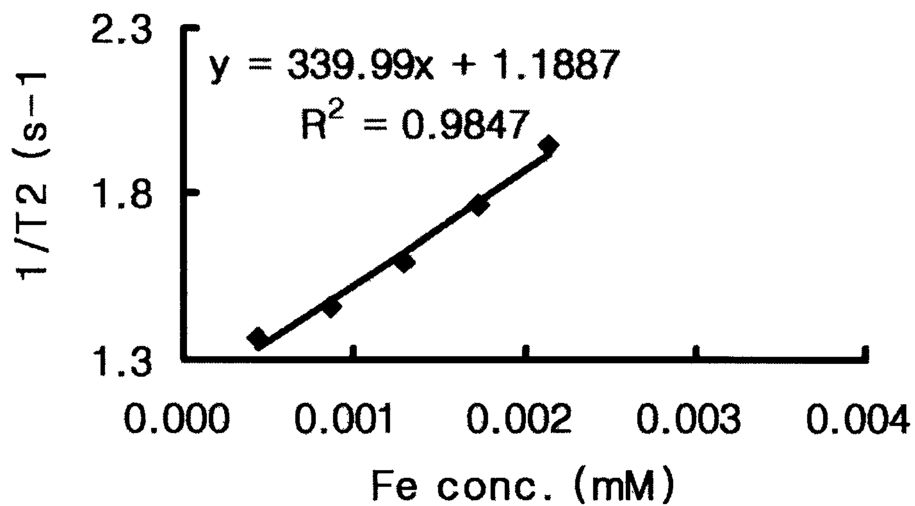
FIG. 10 is a graph showing the results of measuring the R2 relaxivity of an iron oxide nanocapsule encapsulating iron oxide nanoparticles having a size of 15 nm.

FIG. 8 is a graph showing the results of measuring the R2 relaxivity of an iron oxide nanocapsule encapsulating iron oxide nanoparticles having a particle size of 10 nm. It can be seen from FIG. 8 that the R2 relaxivity thereof is 298 $mM^{-1}s^{-1}$. FIG. 9 is a graph showing the results of measuring the R2 relaxivity of an iron oxide nanocapsule encapsulating iron oxide nanoparticles having a particle size of 11 nm. It can be seen from FIG. 8 that the R2 relaxivity thereof is 316 $mM^{-1}s^{-1}$. FIG. 10 is a graph showing the results of measuring the R2 relaxivity of an iron oxide nanocapsule encapsulating iron oxide nanoparticles having a particle size of 15 nm. It can be seen from FIG. 8 that the R2 relaxivity thereof is 340 $mM^{-1}s^{-1}$.

Example 6

Measurement of In-Vivo Magnetic Resonance Relaxivity of Iron Oxide Nanocapsules In order to measure the performance of a magnetic resonance imaging liver contrast agent to iron oxide nanoparticles encapsulated by a carboxymethyldextran-dodecylamine amphiphilic polymer nanocapsule, the in-vivo T2 relaxivity of this nanocapsule was measured using the BGA12 gradient coil of a 4.7 T magnetic resonance imaging apparatus (Biospec 47/40, Bruker Biospin MRI GmbH).

The mouse used for testing was a male Balb/c mouse having a weight of about 20~25 g. The mouse was anesthetized and then horizontally put into an MRI apparatus, and then the coronal plane of the mouse was observed. Further, in order to observe the liver tissue, the mouse was anesthetized over the entire test period, and was thus maintained such that it did not move.

The concentration of iron in the iron oxide nanocapsule was analyzed by ICP-AES, and then 200 μL of the solution was injected into the mouse through the tail vein, and the test was conducted such that the final concentration of the solution was 1 mg Fe/kg which took into consideration the weight of the mouse. The T2 relaxing times thereof were measured using RARE (Rapid Acquisition with Refocused Echoes), and the detailed parameters thereof are shown in Table 2 below.

TABLE 2

| Class. | Parameters | Remark |
|---|---|---|
| TR (Repetition time) | 3,500 ms | |
| TE (Echo time) | 36 ms | 256 times at 8 ms intervals |
| FOV | 60 × 40 mm | |
| Resolution | 0.234 × 0.156 mm/pixel | |
| Slice thickness | 1 mm | |

In order to quantitatively evaluate the T2 attenuation of the iron oxide nanocapsule formed by encapsulating iron oxide nanoparticles in the carboxymethyldextran-dodecylamine conjugate encapsulation material, one section of the liver tissue was selected as a ROI (Region of Interest), and the signal intensity (SI) thereof was analyzed. In order to maximize the reliability of the obtained signal intensity, a 1 wt % agarose solution was charged in a 200 μl tube and then cooled to be solidified, and then the solidified agarose was fixed around the abdominal cavity of the mouse to be used as a control group.

Figure 11:
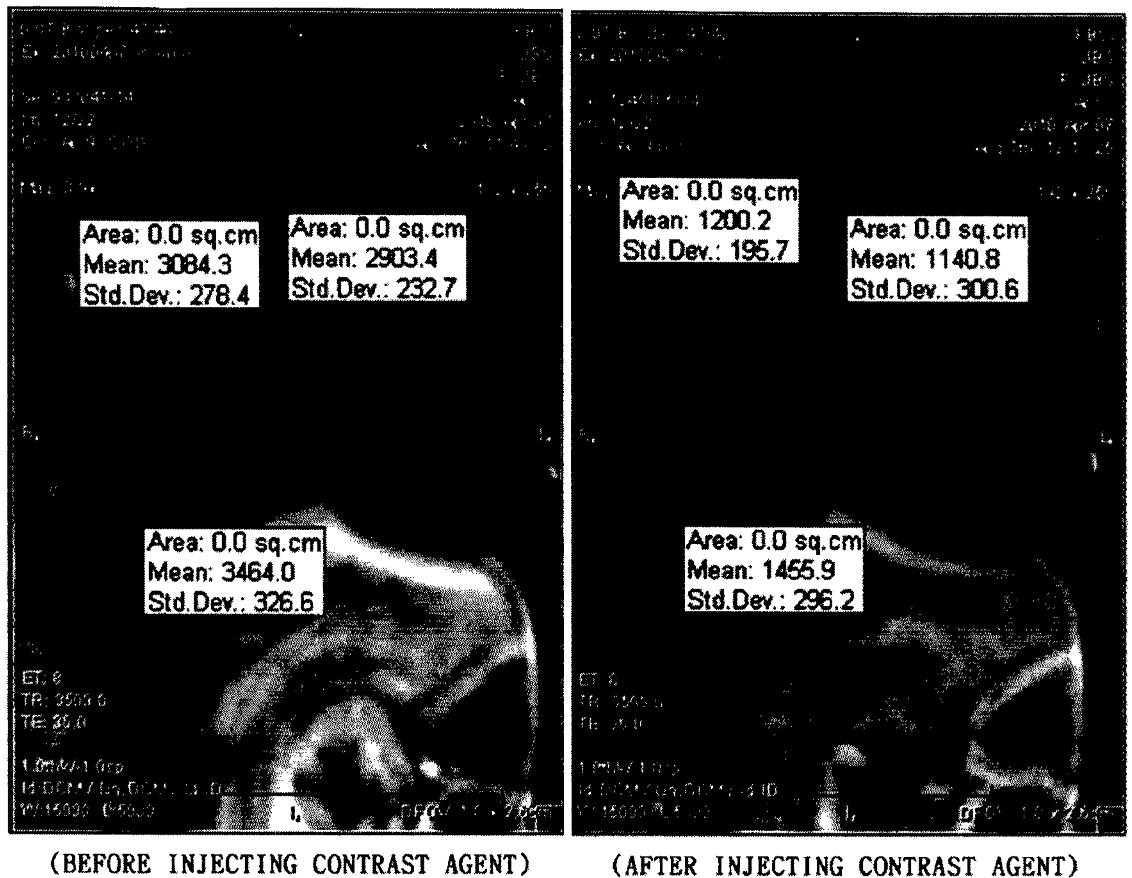
FIG. 11 shows the in-vivo magnetic resonance images using the iron oxide nanocapsules according to the present invention.

FIG. 11 shows the in-vivo magnetic resonance images when the iron oxide nanocapsule manufactured in Example 2 was used as a contrast agent. Comparing the image before injecting the contrast agent with the image after injecting the contrast agent, it can be ascertained that the color of the liver of the mouse was changed to black. As a result, it can be verified that the iron oxide nanocapsule formed by encapsulating iron oxide nanoparticles in the carboxymethyldextran-dodecylamine amphiphilic encapsulation material can be used as a liver contrast agent.

Figure 12:
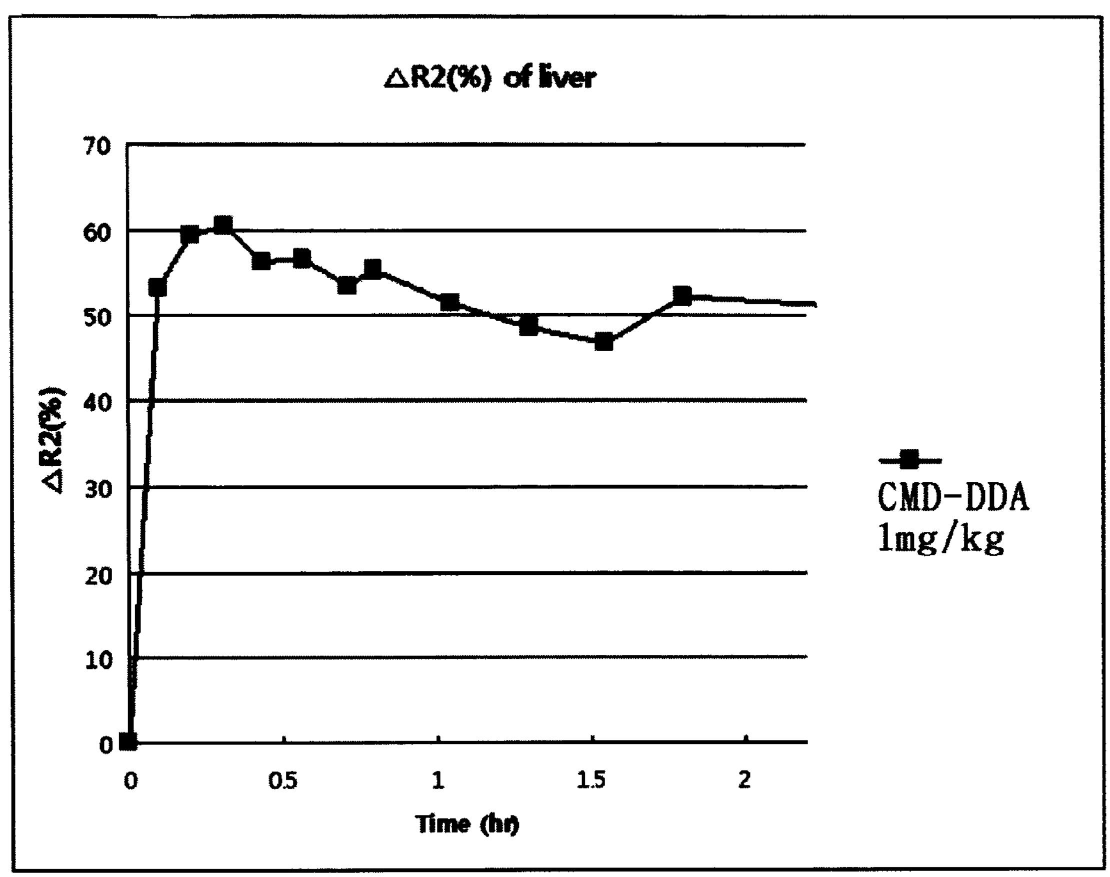
FIG. 12 is a graph showing the relaxivity of iron oxide nanocapsules, obtained by digitalizing the signal values of the liver images measured by the in-vivo magnetic resonance imaging using the iron oxide nanocapsules according to the present invention.

FIG. 12 is a graph showing the relaxivity of the iron oxide nanocapsule, obtained by digitalizing the signal values of the images obtained by measuring the liver using the in-vivo magnetic resonance imaging when the iron oxide nanocapsule manufactured in Example 12 was used as a contrast agent. It is shown in FIG. 12 that the value of ΔR2 was 47~60%.

Comparative Example 1

Encapsulation of Iron Oxide Nanoparticles Using Carboxymethyldextran 120 mg of iron oxide nanoparticles having an average particle size of 10 nm was dispersed in 20 mL of hexane, put into a reactor, and then stirred to obtain an iron oxide nanoparticle solution. 20 mg of carboxymethyldextran was dissolved in 20 mL of distilled water to obtain a carboxymethyldextran solution. When the carboxymethyldextran solution was dropped into the iron oxide nanoparticle solution and then the mixed solution was stirred at 50° C. for 1 hour, the iron oxide nanoparticles existing in the hexane layer of the mixed solution were hydrophilized by carboxymethyldextran and then moved to the water layer thereof, so that the hexane layer became transparent and the water layer became brown, which is the color of iron oxide nanoparticles. Distilled water and ethanol were added to the mixed solution, and then a precipitate was formed using a centrifuge, and then whether or not nanocapsule particles were produced was observed with a transmission electron microscope (TEM).

Figures 13, 14:
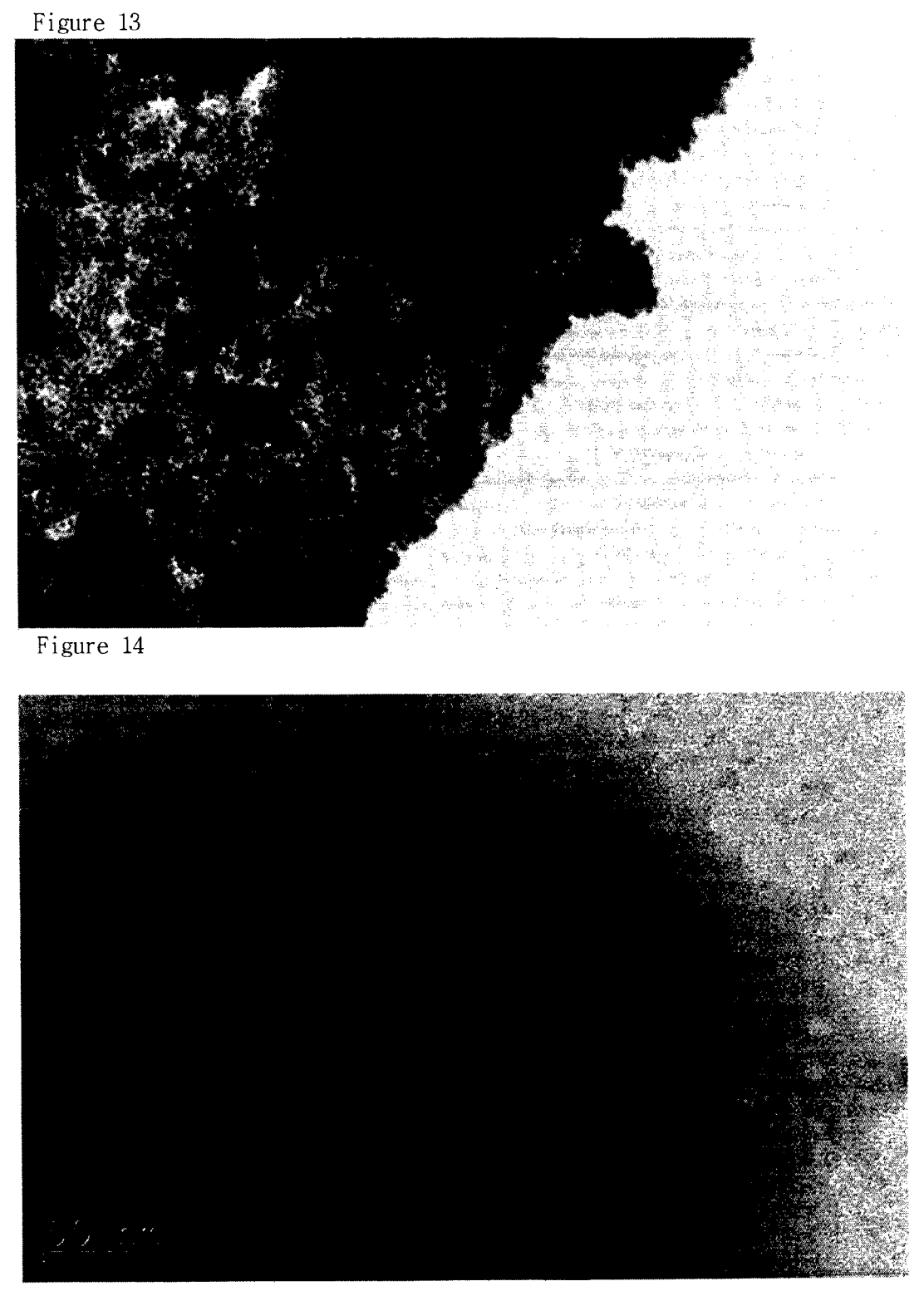

FIG. 13 is a TEM photograph of carboxymethyldextran-iron oxide nanoparticles prepared in this way. As shown in FIG. 13, the carboxymethyldextran-iron oxide nanoparticles were conglomerated, not encapsulated.

From the results, it can be inferred that nanocapsule particles cannot be formed when only carboxymethyldextran, which is a hydrophilic material, is used without using an amphiphilic material.

Comparative Example 2

Encapsulation of Iron Oxide Nanoparticles Hydrophilized by a Surfactant Using Carboxymethyldextran 3 g of SDS (sodium dodecyl sulfate) was dissolved in 18 mL of distilled water, and then this SDS solution was mixed with a solution in which 0.03 g of iron oxide nanoparticles were dissolved in 3 mL of chloroform. Subsequently, chloroform was volatilized from the mixed solution using a vacuum evaporator to obtain a surfactant-coated iron oxide nanoparticle-dispersed solution. 0.01 g of carboxymethyldextran was dissolved in 5 mL of distilled water, and was then dropped into the surfactant-coated iron oxide nanoparticle-dispersed solution. The resultant mixed solution was stirred at 50° C. for 1 hour, and then distilled water and ethanol were added to this solution, and then a precipitate was formed using a centrifuge. In order to accurately observe a polymer, the shapes of particles were observed by TEM.

FIG. 14 is a TEM photograph of the carboxymethyldextran-iron oxide nanoparticles prepared in this way. It can be ascertained from FIG. 14 that iron oxide nanoparticles were encapsulated because the white portion of FIG. 14 represents carboxymethyldextran. However, when the iron oxide nanoparticles were hydrophilized and then encapsulated using a surfactant, not amphiphilic molecules, there is a problem in that it is difficult to control the size of particles, and the dispersion stability of particles becomes poor.

Example 7

Synthesis of Dextran-Linoleic Acid Amphiphilic Conjugate

In order to synthesize a dextran-linoleic acid conjugate, a dextran solution was prepared by completely dissolving 0.8 g of dextran (average molecular weight: 10000) in 50 mL of DMSO, and a linoleic acid solution was prepared by completely dissolving 2.212 mL (7.0 mmol) in 20 mL of DMSO. The two solutions were mixed with each other by dropping the linoleic acid solution into the dextran solution, and then a solution in which 1.12 mL (7.0 mmol) of DCC (n,n'-dicyclohexylcarbodiimide) was dissolved in 20 mL of DMSO and a solution of 0.44 g (3.5 mmol) of DMAP (dimethylaminopyridine) was dissolved in 20 mL of DMSO were added to the mixed solution. This resultant mixed solution was reacted at 25° C. for 24 hours.

Thereafter, the resultant mixed solution was filtered using filter paper, and then an excessive amount of a mixed solution of methanol and acetonitrile mixed at a ratio of 1:2 was added to the filtered mixed solution to produce a light yellow precipitate. This light yellow precipitate was washed with the mixed solution of methanol and acetonitrile mixed at a ratio of 1:2 and then dried three times to obtain a white solid material. This white solid material was dissolved in distilled water, dialyzed, freeze-dried to obtain a solid dextran-linoleic aid conjugate.

Figure 15:
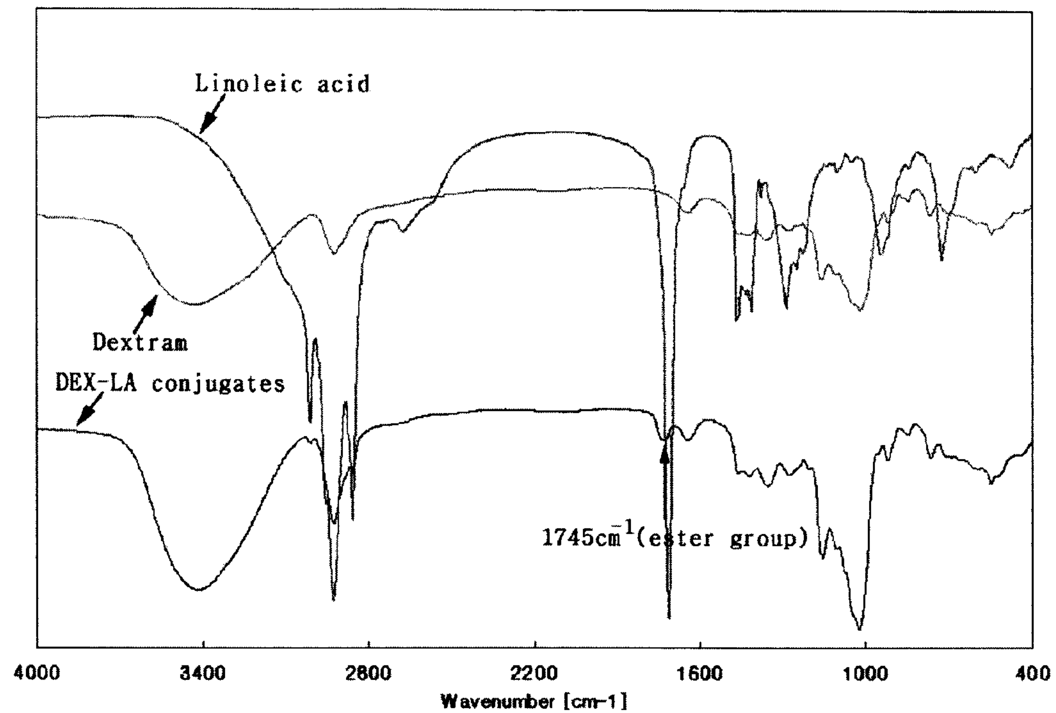
FIG. 15 is a graph showing the results of FT-IR analysis of a carboxymethyldextran-linoleic acid conjugate prepared in Example 7.

FIG. 15 is a graph showing the results of FT-IR analysis of the solid dextran-linoleic aid conjugate. It can be seen that an ester group peak appears at 1745 $cm^{-1}$. Based on this result, it can be ascertained that a dextran-linoleic aid conjugate was successfully synthesized.

Example 8

Encapsulation of Iron Oxide Nanoparticles Using Dextran-Linoleic Aid Conjugate 220 mg of the dextran-linoleic aid conjugate synthesized in Example 7 and 25 ml of PBS were mixed, and then ultrasonically treated for 10 minutes to obtain an aqueous solution of encapsulation material. Further, 22 mg of the iron oxide nanoparticles having an average particle size of 10 nm, prepared in Preparation Example 1, was dispersed in 0.5 mL of chloroform, and then ultrasonically treated for 10 minutes to obtain an iron oxide nanoparticle-dispersed solution. The iron oxide nanoparticle-dispersed solution was dropped into the aqueous solution of encapsulation material (dextran-linoleic aid conjugate solution) at a drip rate of 1 mL/min, and simultaneously these solutions were mixed with each other for 10 minutes using a homogenizer (rpm=26,000) to form nanocapsule particles.

Figure 16:
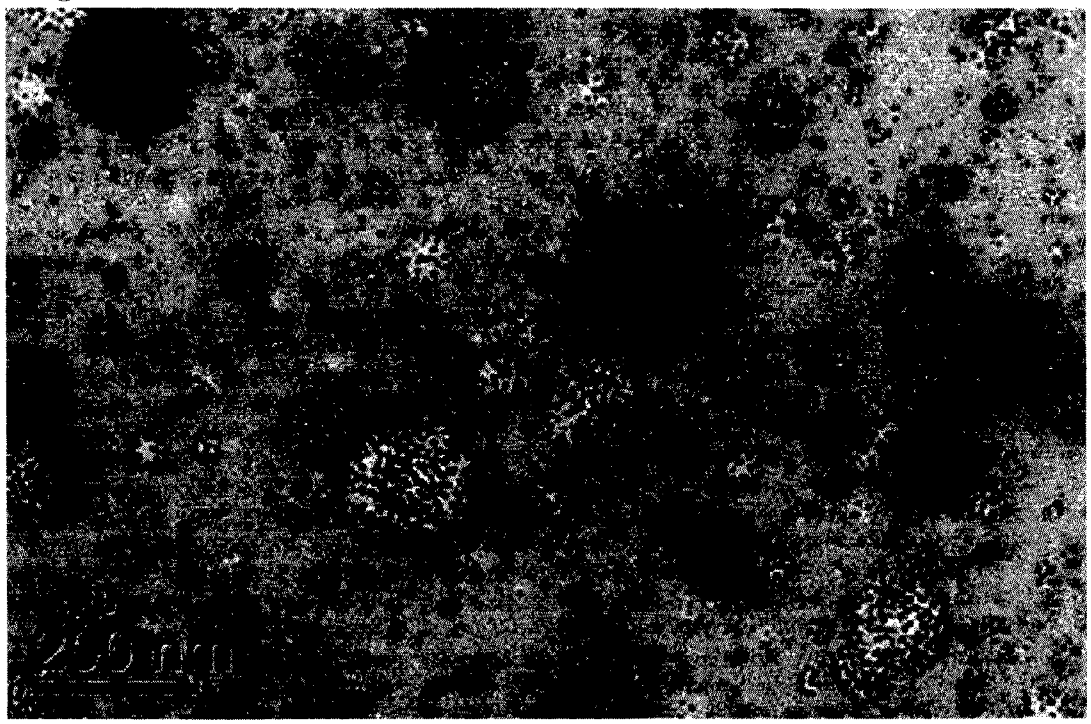
FIG. 16 is a TEM photograph of iron oxide nanocapsules manufactured in Example 8.

FIG. 16 is a TEM photograph of iron oxide nanocapsules, in each of which a plurality of iron oxide nanoparticles are encapsulated by the prepared dextran-linoleic aid conjugate encapsulation material in a state in which they are conglomerated, after negative staining. It can be ascertained from FIG. 16 that iron oxide nanoparticles were encapsulated. The sizes of nanocapsules were measured by dynamic light scattering (DLS). As a result, it was ascertained that the average particle size of the iron oxide nanocapsules was 155 nm.

Example 9

Measurement of In-Vivo Magnetic Resonance Relaxivity of Iron Oxide Nanocapsules In order to measure the performance of the magnetic resonance imaging liver contrast agent of iron oxide nanoparticles encapsulated by the dextran-linoleic aid conjugate nanocapsule, the in-vivo T2 relaxivity of this nanocapsule was measured using the BGA12 gradient coil of a 4.7 T magnetic resonance imaging apparatus (Biospec 47/40, Bruker Biospin MRI GmbH) in the same manner as Example 6.

Figure 17:
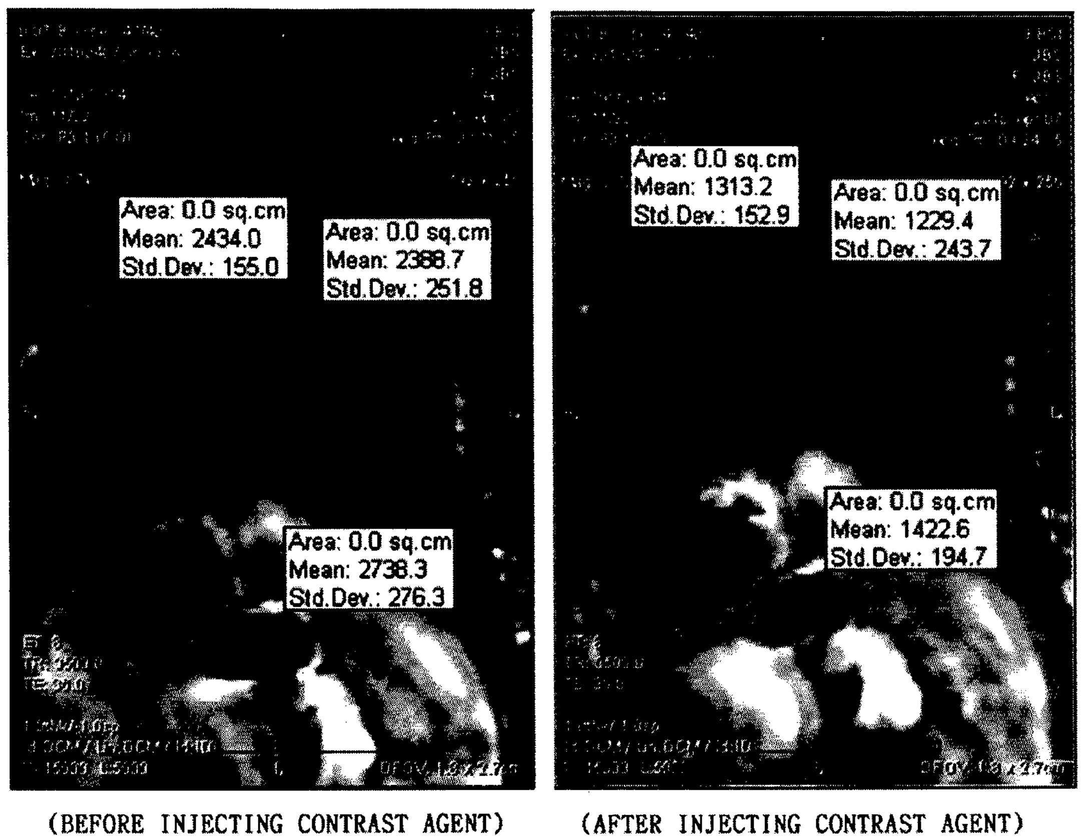
FIG. 17 shows the in-vivo magnetic resonance images using the iron oxide nanocapsules according to the present invention.

FIG. 17 shows the in-vivo magnetic resonance images using the iron oxide nanocapsules. Comparing the image before injecting the contrast agent with the image after injecting the contrast agent, it can be ascertained that the color of the liver of the mouse was changed to black. As a result, it can be verified that the iron oxide nanocapsule formed by encapsulating iron oxide nanoparticles in the dextran-linoleic aid conjugate nanocapsules can be used a liver contrast agent.

Figure 18:
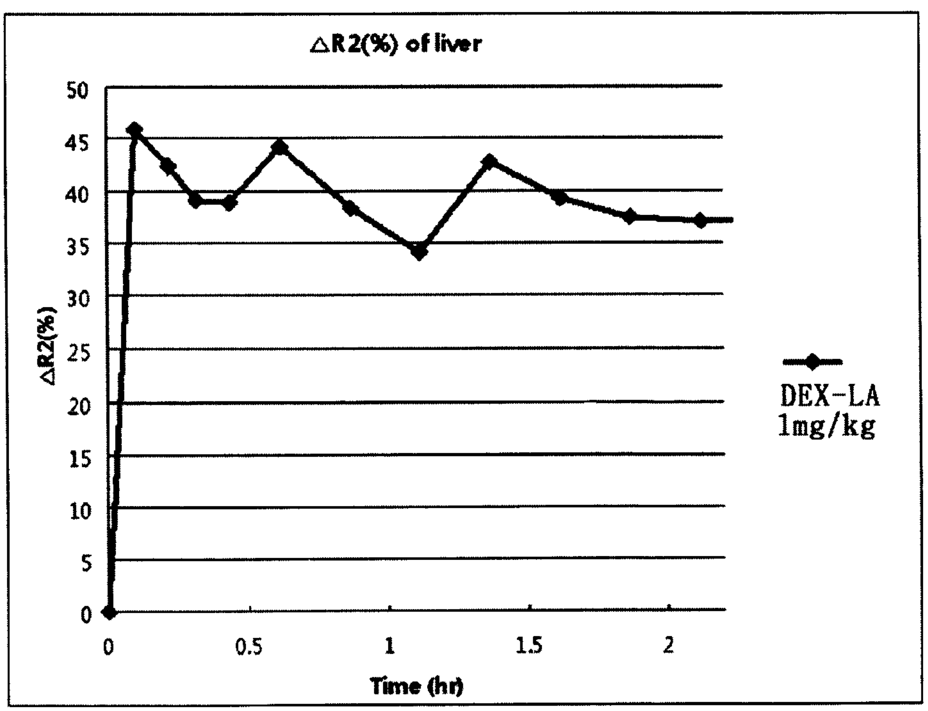
FIG. 18 is a graph showing the relaxivity of iron oxide nanocapsules, obtained by digitalizing the signal values of the liver images measured by the in-vivo magnetic resonance imaging using the iron oxide nanocapsules according to the present invention.

FIG. 18 is a graph showing the relaxivity of iron oxide nanocapsule, obtained by digitalizing the signal values of the images obtained by measuring the liver using the in-vivo magnetic resonance imaging. It is shown in FIG. 18 that the value of $\Delta R2$ was 35~45%.

Comparative Example 3

Encapsulation of Iron Oxide Nanoparticles Using Dextran

The test was conducted in the same manner as Comparative Example 1, except that dextran having a molecular weight of 10000 was used.

Figure 19:
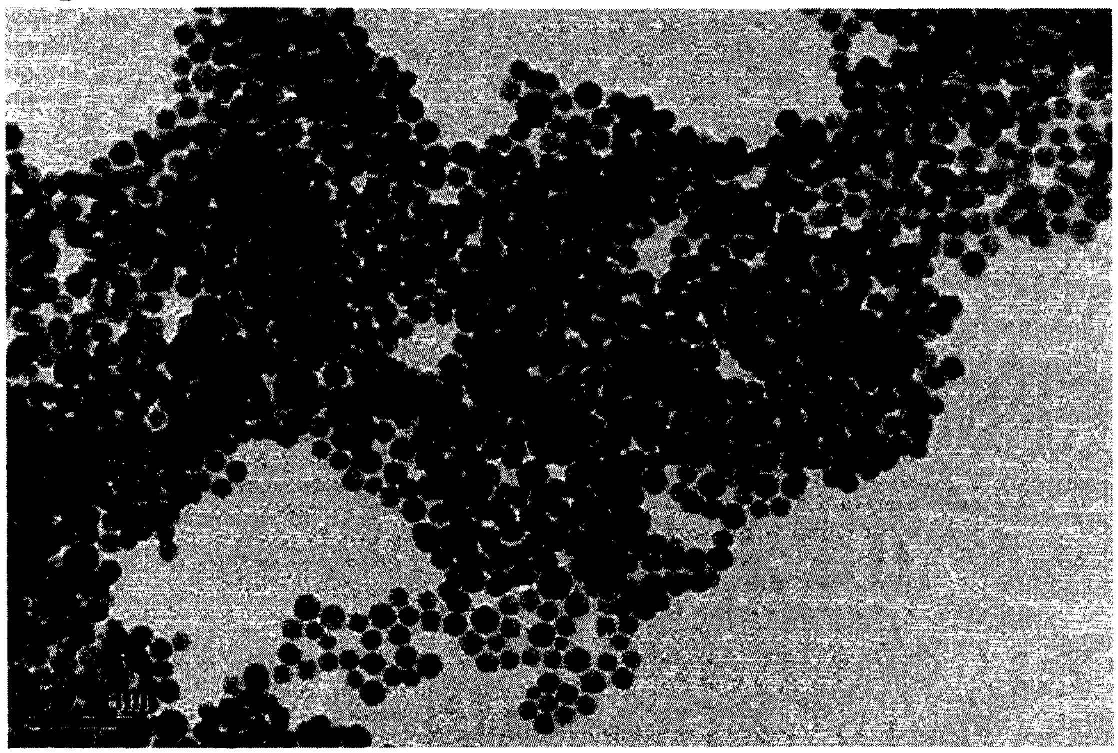
FIG. 19 is a TEM photograph of dextran-iron oxide nanoparticles prepared in Comparative Example 3.

FIG. 19 is a TEM photograph of dextran-iron oxide nanoparticles prepared in this way. As shown in FIG. 19, the dextran-iron oxide nanoparticles were conglomerated, not encapsulated. From the results, it can be inferred that nanocapsule particles cannot be formed when only dextran, which is a hydrophilic material, is used without using an amphiphilic material.

As described above, although the preferred embodiments of the present invention have been disclosed for illustrative purposes, those skilled in the art will appreciate that various modifications, additions and substitutions are possible, without departing from the scope and spirit of the invention as disclosed in the accompanying claims.

Therefore, simple modifications, additions and substitutions of the present invention belong to the scope of the present invention, and the specific scope of the present invention will be clearly defined by the appended claims.

The invention claimed is:

1. A method of manufacturing an iron oxide nanocapsule, comprising the steps of:

thermally decomposing an iron complex to prepare hydrophobic ligand-bonded iron oxide nanoparticles; and encapsulating the hydrophobic ligand-bonded iron oxide nanoparticles by a carboxymethyldextran-dodecylamine conjugate encapsulation material or a dextran-linoleic acid conjugate encapsulation material to form an iron oxide nanocapsule.

2. The method of claim 1, further comprising the steps of:

a) preparing a carboxymethyldextran-dodecylamine conjugate encapsulation material represented by Formula 1 below or a dextran-linoleic acid conjugate encapsulation material represented by Formula 2 below;

b) thermally decomposing an iron complex in which a hydrophobic organic acid group of $C_4$ to $C_{25}$ as a ligand is bound to iron as a central atom to prepare hydrophobic ligand-bonded iron oxide nanoparticles;

c) dissolving the encapsulation material in a buffer solution to prepare an aqueous solution of encapsulation material, and dispersing the iron oxide nanoparticles in an organic nonpolar solvent to prepare a nanoparticle-dispersed solution;

d) dropping the nanoparticle-dispersed solution into the aqueous solution of encapsulation material and stirring a mixed solution of the aqueous solution of encapsulation material and the nanoparticle-dispersed solution to prepare an iron oxide nanocapsule-dispersed solution in which iron oxide nanocapsules each encapsulating a plurality of the iron oxide nanoparticles are dispersed; and e) removing the organic nonpolar solvent from the iron oxide nanocapsule-dispersed solution by volatilization to prepare a water-dispersed iron oxide nanocapsule solution,

[Formula 1]

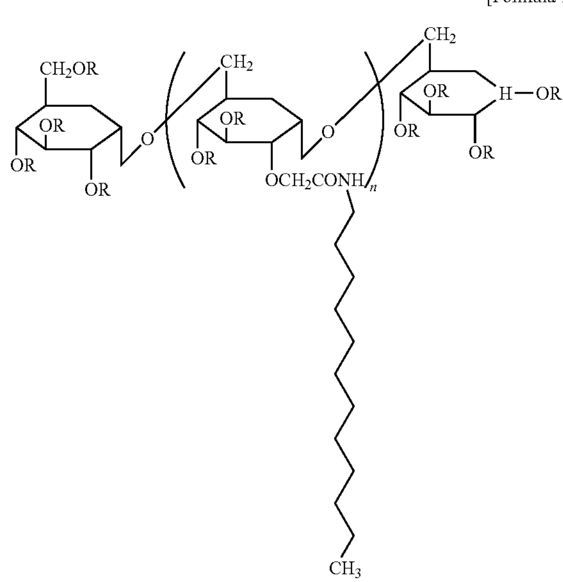

wherein R is H or $CH_2COOH$, and n is an integer of 1 to 5000,

[Formula 2]

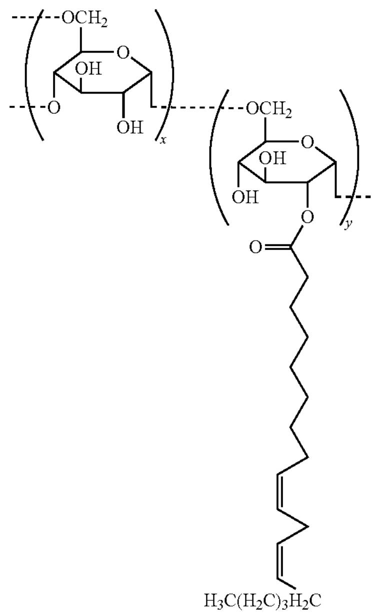

wherein x is an integer of 1 to 1000, and y is an integer of 1 to 1000.

3. The method of claim 2, wherein the encapsulation material is a carboxymethyldextran-dodecylamine conjugate, and the step a) includes the steps of:

a1-1) mixing a carboxymethyldextran solution with a dodecylamine solution to form a first mixed solution;

a1-2) adding 1-ethyl-3-(3-dimethylaminopropyl)carbodiimide (EDC) and n-hydroxysuccinicimide (NHS) to the first mixed solution to form a second mixed solution; and a1-3) dialyzing, and then freeze-drying the second mixed solution.

4. The method of claim 2, wherein the encapsulation material is a dextran-linoleic acid conjugate, and the step a) includes the steps of:

a2-1) mixing a dextran solution with a linoleic acid solution to form a first mixed solution;

a2-2) adding n,n'-dicyclohexylcarbodiimide (DCC) and dimethylaminopyridine (DMAP) to the first mixed solution to form a second mixed solution; and a2-3) dialyzing, and then freeze-drying the second mixed solution.

5. The method of claim 3, wherein the carboxymethyldextran has an average molecular weight of 500 to 1,000,000 Da.

6. The method of claim 3, wherein the carboxymethyldextran solution is prepared by adding dimethyl sulfoxide (DMSO) to an aqueous carboxymethyldextran solution in which carboxymethyldextran is mixed with water at a ratio of 1:3-5 by weight, the dimethyl sulfoxide (DMSO) being added in an amount of 10 to 15 times that of water in the aqueous carboxymethyldextran solution by weight.

7. The method of claim 6, wherein the dodecylamine solution includes dodecylamine, chloroform and dimethyl sulfoxide (DMSO) at a mixing ratio of 1:8-12:25-35 by weight.

8. The method of claim 7, wherein the carboxymethyldextran solution is mixed with the dodecylamine solution such that a ratio of dodecylamine:carboxymethyldextran is 1:1-10 by weight.

9. The method of claim 7, wherein the dodecylamine, EDC and NHS are added such that a ratio of dodecylamine:EDC:NHS is 1:0.3-0.7:0.1-0.4 by weight.

10. The method of claim 4, wherein the dextran has an average molecular weight of 100 to 150,000 Da.

11. The method of claim 4, wherein the dextran solution is a solution in which dextran is mixed with dimethyl sulfoxide (DMSO) at a ratio of 1:50-80 by weight, and the linoleic acid solution is a solution in which linoleic acid is mixed with dimethyl sulfoxide (DMSO) at a ratio of 1:8-14 by weight.

12. The method of claim 11, wherein the dextran solution is mixed with the linoleic acid solution such that a ratio of dextran:linoleic acid is 1: 2-5 by weight.

13. The method of claim 12, wherein the dextran, DCC and DMAP are added such that a ratio of dextran:DCC:DMAP is 1:1.5-2:0.3-0.8 by weight.

14. The method of claim 2, wherein, in the step c), the buffer solution is a phosphate buffered saline (PBS), and the organic nonpolar solvent is chloroform.

15. The method of claim 13, wherein, in the step d), the iron oxide nanoparticle-dispersed solution is dropped into the aqueous solution of encapsulation material at a drip rate of 0.1-3 mL/min.

16. The method of claim 13, wherein the aqueous solution of encapsulation material is a solution in which the encapsulation material is mixed with the buffer solution at a ratio of 1:50-500 by weight, and the nanoparticle-dispersed solution is a solution in which the iron oxide nanoparticles are mixed with the organic nonpolar solvent at a ratio of 1:10-100 by weight.

17. The method of claim 15, wherein, in the step d), the aqueous solution of encapsulation material is stirred at a rotational speed of 20000-30000 rpm.

18. An iron oxide nano capsule, manufactured by the method of claim 1.

19. A magnetic resonance imaging (MRI) contrast agent, comprising the iron oxide nanocapsule manufactured by the method of claim 1.

* * * * *

UNITED STATES PATENT AND TRADEMARK OFFICE

CERTIFICATE OF CORRECTION

PATENT NO. : 9,028,875 B2
APPLICATION NO. : 13/818734
DATED : May 12, 2015
INVENTOR(S) : Eun Byul Kwon et al.

It is certified that error appears in the above-identified patent and that said Letters Patent is hereby corrected as shown below:

In the Claims

Column 17, Line 17, Claim 15, delete “13,” and insert -- 14, --

Column 18, Line 3, Claim 16, delete “13,” and insert -- 14, --

Column 18, Line 13, Claim 18, delete “nano capsule,” and insert -- nanocapsule, --

Signed and Sealed this
Twenty-second Day of December, 2015

Michelle K. Lee
*Director of the United States Patent and Trademark Office*